United States Patent [19]
Koutavas

[11] Patent Number: 5,380,199
[45] Date of Patent: Jan. 10, 1995

[54] DENTAL ARTICULATOR

[76] Inventor: Ioannis Koutavas, 5-9 Vapheiochoriou Street, GR-114 76 Athens, Greece

[21] Appl. No.: 50,070
[22] PCT Filed: Jun. 10, 1992
[86] PCT No.: PCT/GR92/00007
 § 371 Date: Apr. 27, 1993
 § 102(e) Date: Apr. 27, 1993
[87] PCT Pub. No.: WO93/01762
 PCT Pub. Date: Feb. 4, 1993

[30] Foreign Application Priority Data

Jul. 17, 1991 [GR] Greece .............. 910100316

[51] Int. Cl.⁶ .............................................. A61C 11/00
[52] U.S. Cl. .................................. 435/65; 433/60; 433/63
[58] Field of Search ............... 433/57, 58, 60, 61, 433/63, 65

[56] References Cited

U.S. PATENT DOCUMENTS

| 582,731 | 5/1897 | Fourt | 433/58 |
| 2,262,574 | 11/1941 | Chott | 433/57 |
| 3,844,040 | 10/1974 | Willis | 433/60 |
| 4,175,325 | 11/1979 | Beckwith | 433/60 |
| 4,299,570 | 11/1981 | Yogosawa | 433/60 |
| 4,414,822 | 1/1993 | Blechner | 433/60 |
| 4,496,320 | 1/1985 | Hwang | 433/54 |
| 5,026,282 | 6/1991 | Koike | 433/58 |

Primary Examiner—John J. Wilson
Attorney, Agent, or Firm—Herbert Dubno

[57] ABSTRACT

A dental articulator has both a base and head enabling gnatho-condylar movements and locking by threaded screws. The movable members receive disposable rubber holders which can allow direct contact with plaster of the casts, anchoring of the casts by screws through stoppers on the holders or by embedding the holders which are disposable and rubber in the cast. The column has a post which can be locked at adjustable heights relative to the base.

3 Claims, 3 Drawing Sheets

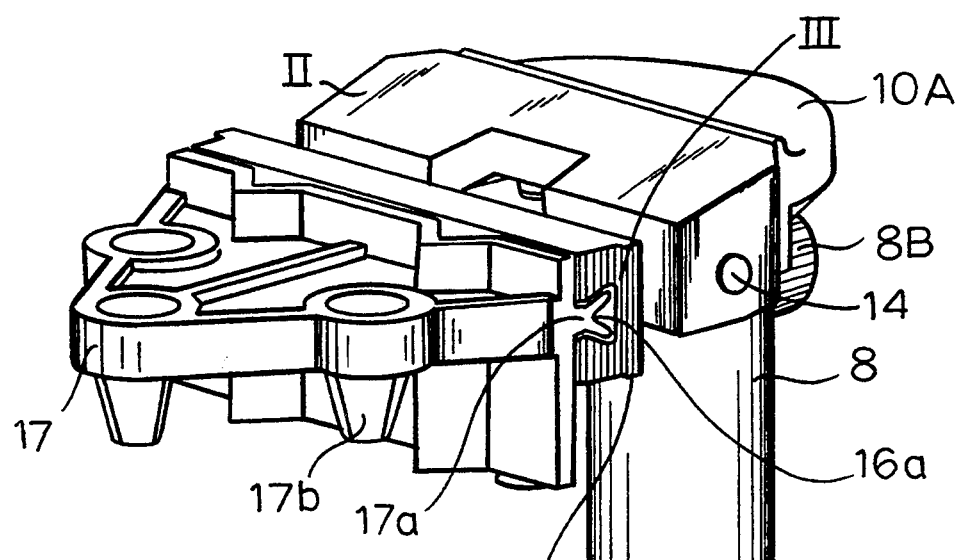
FIG.1
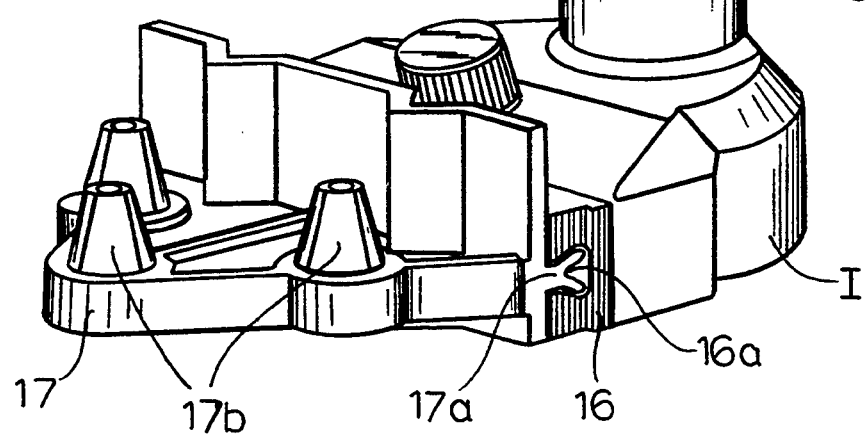
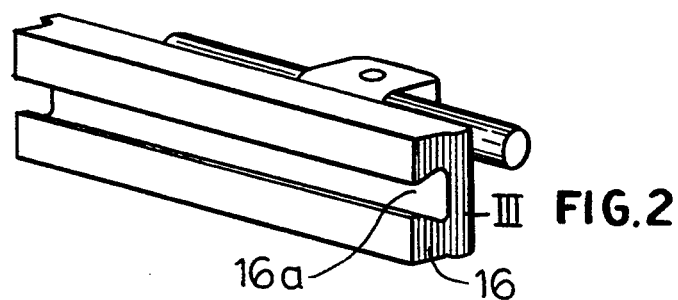
FIG.2
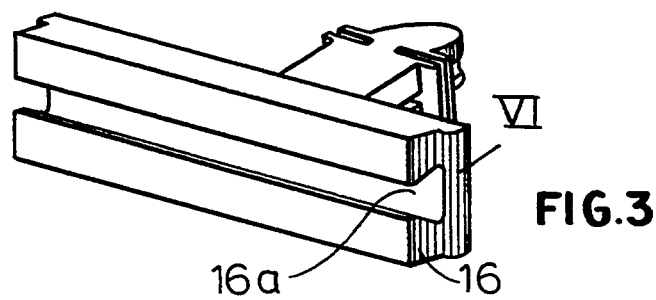
FIG.3

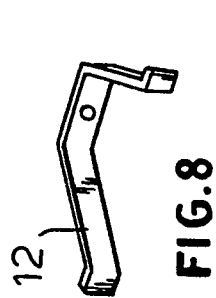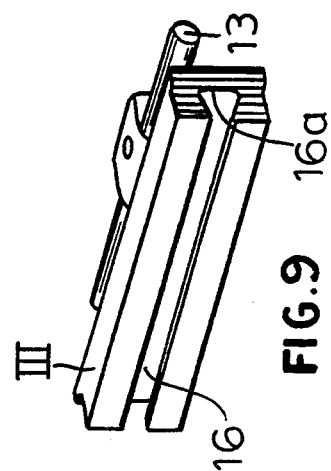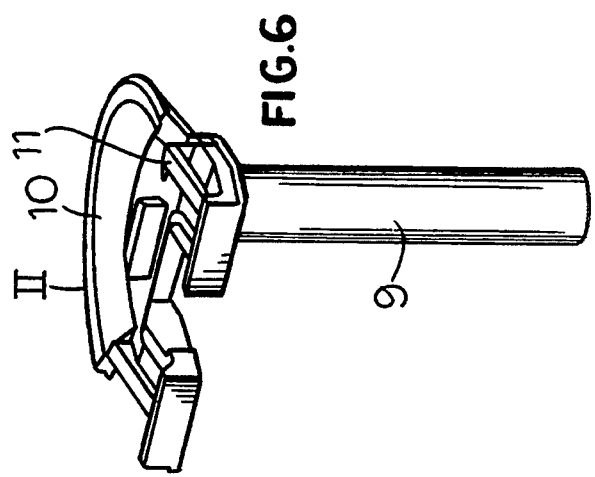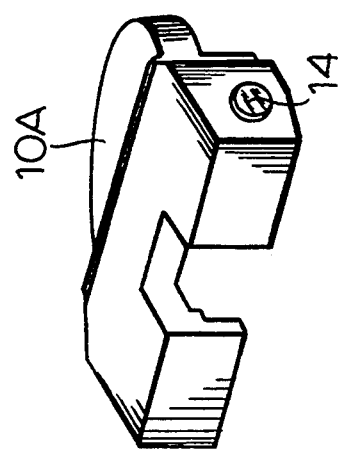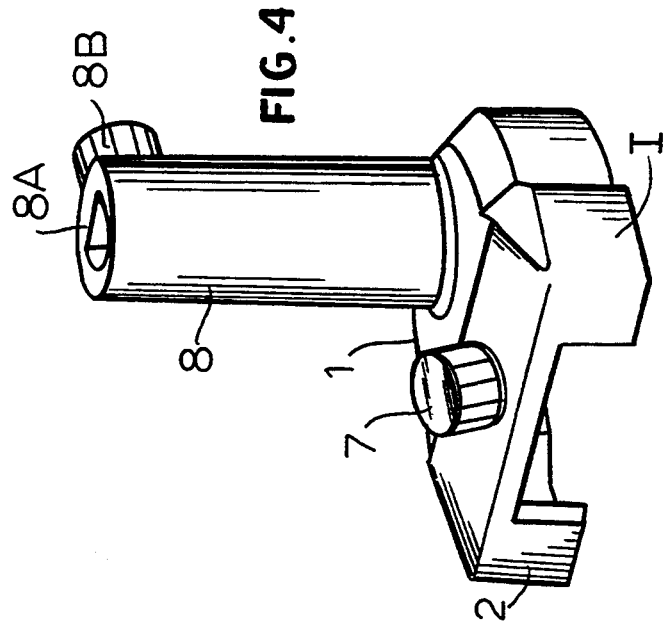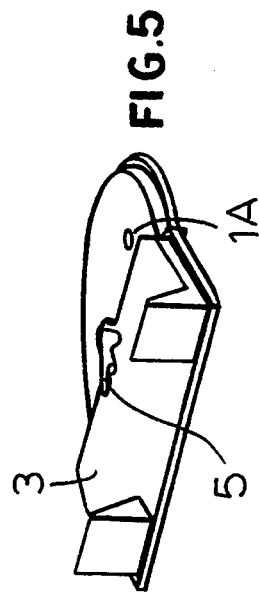

DENTAL ARTICULATOR

CROSS REFERENCE TO RELATED APPLICATIONS

This application is a national phase of PCT/GR 92/00007 filed Jun. 10, 1992 and based, in turn, upon Greek national application 910100316 filed Jul. 17, 1991 under the International Convention.

1. Field of the Invention

My present invention relates to a plane line dental articulator to be used in mounting dental casts in dental prosthesis laboratories.

2. Background of the Invention

Plane line dental articulators used in dentistry to date are known and classified as follows:

a. articulators in which the mounting of the dental casts is carried out by means of gypsum.

b. articulators in which the mounting of the dental casts is carried out without gypsum.

Additionally, both articulators mentioned above sibilate the movements of the lower jaw on the upper element of the articulator, a position that does not match the normal function of the parts of the oral cavity.

The various models of the first case manufactured to date are of one size and nonadjustable with relation to the height of dental casts. Therefore, the mounting of the casts is carried out directly on the metallic frame by means of gypsum.

This has the following drawbacks:

a. Sensitivity to dimensional changes in the gypsum used in cast mounting. That causes distortion of the articulation due to the fact that this kind of articulator cannot be adjusted with relation to the height of the dental casts. Furthermore, there is no guide for setting the specific quantity of gypsum used in the mounting of upper and lower jaw casts.

b. The articulator is hard to handle as the operator must hold the articulator frame together with the mounted casts during prosthodontic work.

c. The removal of the casts from the articulator is carried out by breaking the gypsum. This can jeopardize the integrity of the casts and reduce the strength of the articulator.

d. Most plane line articulators can be used only for a single case each time because the casts are mounted directly on the metallic frame.

The second type of articulator (namely, articulators in which the mounting of the casts is carried out without gypsum) have not fully remedied these drawbacks. It is for this reason that to date the majority of the articulations are formed on articulators by means of gypsum.

The problems raised by the second type of articulator are the following:

a. Time consuming process for mounting the casts on the articulator due to that the systems currently in use require an additional process of manipulating the casts and a specific type of mold which increases the size of the cast and make it unwieldy.

b. The mechanical process for mounting the cast which is used is not safe nor firm, two factors necessary for the accuracy of the oral cavity articulation and for the prosthodontic work. The mechanical means are bulky and heavy and not easy to work with.

c. Owing to the above stated difficulties, the various systems that have been used so far cannot offer a solution to an entire range of cases, but have limited utility.

Object of the Invention

It is an object of the invention to remedy these drawbacks. More particularly, it is an object to provide an improved articulator which allows the movements of the lower jaw take place in the area of the lower element of the articulator and which replaces all complicated cast mounting systems with a simple one.

Summary of the Invention

According to the invention to secure accurate movements on the articulator and the harmonization thereof with the normal movements of the lower jaw, the new articulator provides a new system located on the lower element of the articulator which executes the movements while making available the upper element of the articulator for the same movements of the lower jaw.

By a triple function rubber sleeve-stopper and holder, the dental articulator can be applied to cases of cast mounting with or without gypsum.

The arcticulator of the invention offers a solution of the problem of adjusting the articulator with relation to the height of the cast, because its new design is based on a vertical guide meant for the vertical movement of the upper element of the articulator which can be adjusted depending on the height of the dental cast.

The mounting of the dental casts on the articulator by means of gypsum is carried out on the disposable rubber sleeve-stopper and not directly on the metallic frame, thereby facilitating the removal and exact remounting of the casts thereon.

The use of the sleeve-stoppers prevents the gypsum from dimensional changes because the stoppers, which are rubber pins built into the sleeve-stoppers, come into direct contact with the casts which they support during their mounting on the articulator and limit to a minimum any dimensional change. The stoppers function also as guiding points determining an even gypsum quantity used for the mounting of the casts on the upper and lower jaw.

Thanks to the use of the disposable rubber sleeve-stopper-holder on the metallic drives of the articulator, the same articulator can be used in multiple dental cases provided that a new rubber sleeve-stopper-holder is mounted thereon for each use. The dental casts can be stored for later use of the articulator without any occlusion in the articulation.

The problems solved by the articulator by comparison to the second type of plane line articulators are the following:

The mounting of the casts is fully controlled thanks to the double function sleeve-holder, which first is mounted on the metallic drives of the articulator, and the screwing system (holders). The holder holds the cast firmly as it penetrates the cast at its center. The holders are blind and destined to prevent the cast from circular displacement.

Additionally, the sleeve-stopper system can be mounted and built directly into the case, thereby enabling an automatic mounting of the cast on the articulator.

The advantages offered by the present invention are the following:

a. The double movement system of the lower jaw. For the movement thereof the operator has the choice of either the upper element or the lower element of the articulator.

b. The triple function sleeve-stopper-holder can be applied to both types and this is made possible by the different use of the sleeve-stopper-holder.

c. The articulator can be adapted in accordance with the height of the dental casts.

d. The sleeve-stoppers used in the mounting of the casts on the articulator the stoppers hold the casts firmly and prevent the gypsum from dimensional changes.

FIG. 1 is a perspective view of the articulator with the rubber double-function sleeve-stoppers adapted to the metallic drives of the upper and lower element of the articulator.

FIG. 2 is a perspective view of an upper element of the articulator;

FIG. 3 is a perspective view of the lower element of the articulator.

FIG. 4 is a perspective view showing the base and column of the articulator of FIG. 1;

FIG. 5 is a perspective view of the lower articulator place received in the socket of the base;

FIG. 6 is a perspective view of a portion of the head and the post receivable in the column of FIG. 4;

FIG. 7 is a perspective view of the upper member of the head;

FIG. 8 is a perspective view of a spring structure receivable in the head and controlling the movement of the upper mounting member;

FIG. 9 is a perspective view corresponding to FIG. 2 showing the upper mounting member;

Specific Description

The support of the articulator comprises the base 1 with a socket 2 (FIG. 4) receiving two gnatho-condylar pathways 3 on either side with an inclination of 15° each. A plate 1a is attached thereto (FIG. 5).

Figure 12:
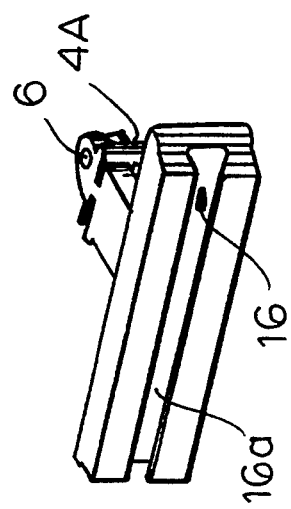
FIG. 12 is a perspective view of the lower mounting member cooperating with the springs of FIG. 11 and cooperating with the plate of FIG. 5.

An arrow-like passage 5 is located at the bottom of the articulator base plate 1A. The base socket 2 is destined to hold the lower element (component IV, FIG. 12) with the vertical guiding axis 6 which is located at the starting point of the arrow-like passage 5.

Figure 13:
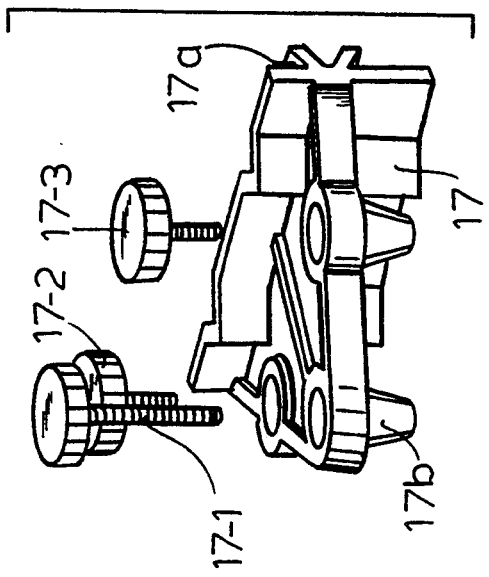
FIG. 13 is a perspective view of the upper disposable rubber holder and the screws cooperating therewith.
Figure 14:
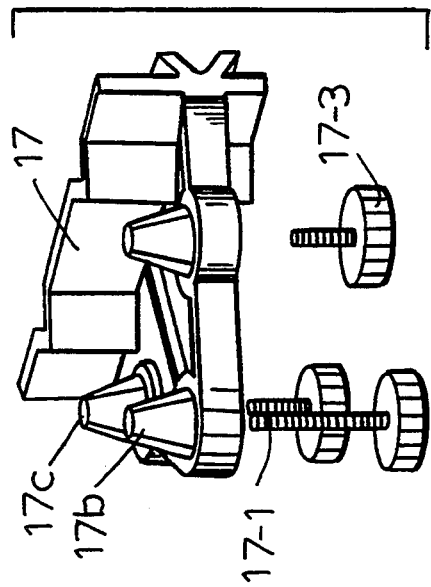
FIG. 14 is a perspective view of the lower disposable rubber holder and the screws cooperating therewith.
Figure 15:
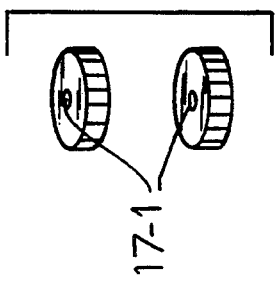
FIG. 15 is a perspective view of the nuts which engage the latter screws when, in accordance with one mode of the invention, the casts are secured to the holders by these screws.
Figure 10:
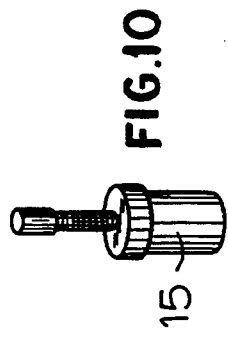
FIG. 10 is a perspective view of the locking screw means for the upper mounting member.
Figure 11:
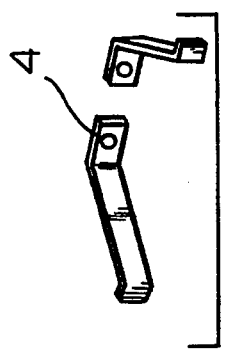
FIG. 11 is a perspective view of the springs for responding to the movement of the lower mounting member.

The arrow-like passage 5 and the articulator base 1, the guiding axis 6 of component IV and the gnatho-condylar springs 4 (FIG. 11) on the gnatho-condylar pathways 3 are the means by the gnatho-condylar movements of the lower jaw, lateral and protrusive are set.

When the lower element of the articulator is not used for the lower jaw movements, it can be immobilized by the securing means 7 which screws component IV, i.e. the lower element of the articulator against the articulator base plate 1A.

The securing point is determined by the position of the axis 6 when at the starting point, i.e. at the top of arrow-like passage. This position symbolizes the centric occlusion of the articulation.

The articulator base 1 also has a carrier column 8; the axial carrier post 9 is inserted in the column. The carrier post 9 is fixed on the head 10 of component II of the articulator. The carrier column 8 of the base 1, the axial carrier post 9 and the head 10 are intended to determine the vertical movement of components II and III of the articulator; this is made possible owing to the passage 8A in the carrier column 8 of the base 1 and is secured by means of the threaded screw 8B.

The head 10 of component II of the articulator supports the two gnatho-condylar tracks 11 each of 15° and a gnatho-condylar plate 12 at each gnatho-condylar track; the parts along with the axis 13 of component III are meant for the movement of the upper element of the articulator.

When the upper element of the articulator III is not used to perform the movements (lateral and protrusive), it is secured by the securing means or screw 14 at a point determined by the starting point of the axis and the gnatho-condylar plates which are in fact the frontal part of the gnatho-condylar tracks, the point is the centric occlusion of the articulation.

A screw along vertical dimension axis 15 extends into the lower part of the head 10, the screw regulating the inclination of the upper element of the articulator with relation to the base; this simulates the vertical dimension of the oral cavity.

The sleeve-stopper-holders 17 have dovetails which are inserted in the metallic dovetail grooves of bars 16 of components III and IV of the upper and lower element of the articulator. The mounting of dental casts is done on the sleeve-stopper-holders.

The frustoconical rubber pins and the sleeve-stopper-holders 17 have three functions:

a. they are used for the direct mounting of casts by means of gypsum in which case the three rubber pins act as stoppers or plugs fitted in the plaster, i.e. they limit to minimum the dimensional change of gypsum while holding firm the casts during solidification of gypsum.

b. in the second case the three rubber pins form passages; three screwing holders (17-1, 17-2, 17-3) pass through the pins and hold the cast firm without any use of gypsum.

c. in the third case, the sleeve-stopper-holder 17 can be directly built into the cast during manufacturing; in this way the case is mounted on the articulator by the dovetail formations.

I claim:

1. A dental articulator, comprising:
   a base;
   a hollow column affixed to said base and extending upwardly therefrom, said base forming a socket;
   a lower articulation plate received in said socket and provided with gnatho-condylar formations determining gnatho-condylar, lateral and protrusive lower jaw movements;
   a lower mounting member of metal mounted on said lower articulation plate for said lower jaw movements relative thereto, said lower mounting member having a generally horizontal dovetail formation;

first locking screw means cooperating with said lower mounting member for locking same in position relative to said base and said lower articulation plate;

a first disposable rubber holder having a dovetail formation complementary to and mating with said dovetail formation of said lower mounting member and removably receivable therein;

a post slidably received in said column and vertically adjustable therein;

second locking screw means on said column for locking said post at an adjusted height relative to said column;

a head formed on said post and provided with gnatho-condylar formations defining gnatho-condylar movements on said head;

an upper mounting member of metal mounted on said head for jaw movements relative thereto, said upper mounting member having a generally horizontal dovetail formation;

third locking screw means cooperating with said upper mounting member for locking same in position relative to said head; and a second disposable rubber holder having a dovetail formation complementary to and mating with said dovetail formation of said upper mounting member and removably receivable therein, each of said rubber holders being directly in contact with plaster of respective casts, having passages traversable by screws for mounting respective casts on said holders, and being incorporatable bodily in respective casts in alternative modes of mounting casts on said holders.

2. The dental articulator defined in claim 1 wherein each of said holders is provided with a plurality of frustoconical plugs having throughgoing passages receiving said screws.

3. The dental articulator defined in claim 1 wherein said formations in said plate include an arrow-shaped passage.

* * * * *